(12) United States Patent
Kuwano et al.

(10) Patent No.: US 8,859,249 B2
(45) Date of Patent: Oct. 14, 2014

(54) PROCESS OF TREATMENT FOR OXIDIZING AN ACIDIC SOLUTION CONTAINING AN IODIDE ION AND AN IRON (II) ION

(75) Inventors: Kenichi Kuwano, Hitachi (JP); Akira Miura, Hitachi (JP)

(73) Assignee: JX Nippon Mining & Metals Corporation, Tokyo (JP)

( * ) Notice: Subject to any disclaimer, the term of this patent is extended or adjusted under 35 U.S.C. 154(b) by 9 days.

(21) Appl. No.: 13/418,654

(22) Filed: Mar. 13, 2012

(65) Prior Publication Data
US 2012/0237995 A1 Sep. 20, 2012

(30) Foreign Application Priority Data

Mar. 14, 2011 (JP) ................. 2011-055594

(51) Int. Cl.
*C12P 3/00* (2006.01)
*C12P 1/04* (2006.01)
*C12N 11/00* (2006.01)
*C12N 11/14* (2006.01)
*C02F 3/34* (2006.01)
*C22B 15/00* (2006.01)
*C22B 3/44* (2006.01)
*C22B 3/18* (2006.01)
*C12M 1/12* (2006.01)

(52) U.S. Cl.
CPC ... *C12P 3/00* (2013.01); *C22B 3/44* (2013.01); *C12N 11/00* (2013.01); *C12M 25/20* (2013.01); *C22B 3/18* (2013.01); *C22B 15/0069* (2013.01); *C12N 11/14* (2013.01)
USPC .......... 435/168; 435/170; 435/174; 435/176; 435/262; 423/27; 75/743

(58) Field of Classification Search
CPC ............. C22B 3/0098; C22B 15/0069; C22B 15/0071; C22B 15/0067; C22B 3/08; C22B 15/00; C22B 11/00; C02F 3/346; C02F 1/766; C02F 3/34; C12P 3/00; C12P 1/04; C12N 11/14; C12N 11/00; C12M 25/20
See application file for complete search history.

(56) References Cited

U.S. PATENT DOCUMENTS

| | | | |
|---|---|---|---|
| 5,914,441 A * | 6/1999 | Hunter et al. ................... 75/712 |
| 6,506,935 B1 * | 1/2003 | Kulprathipanja et al. .... 562/608 |
| 2010/0018349 A1 | 1/2010 | Manabe |
| 2010/0206009 A1 | 8/2010 | Moon et al. |
| 2011/0041654 A1 * | 2/2011 | Manabe .......................... 75/743 |
| 2011/0045581 A1 * | 2/2011 | Collao Olivares et al. 435/293.1 |
| 2011/0229385 A1 | 9/2011 | Kuwano et al. |

FOREIGN PATENT DOCUMENTS

| | | |
|---|---|---|
| JP | 47-38981 | 10/1972 |
| JP | 2010-189258 A | 9/2010 |
| JP | 2011-42858 A | 3/2011 |
| JP | 2011-190520 A | 9/2011 |
| WO | WO 2011/145688 A1 | 11/2011 |

OTHER PUBLICATIONS

Nemati et al., Appli. Microbiol. Biotechnol., 46:250-255, 1996.*
Australian Office Action issued Nov. 7, 2012 in corresponding Australian patent application No. 2012201341.

* cited by examiner

*Primary Examiner* — Jennifer McDonald
*Assistant Examiner* — Qing Xu
(74) *Attorney, Agent, or Firm* — Birch Stewart Kolasch & Birch, LLP

(57) ABSTRACT

A method for producing an iron (III) ion from the acidic solution containing an iodide ion and an iron (II) ion efficiently and stably is provided. The method including performing the following steps (a)-(b), repeatedly and continuously: (a) a step wherein the iron (II) ion in the acidic solution containing the iodide ion and the iron (II) ion is oxidized into iron (III) ion in a reactor using a microbes immobilizing carrier to which iron oxidizing microbes attached; (b) a step wherein sedimentation of the solution obtained in the step (a) is performed in a sedimentation tank to obtain the solution containing the iron (III) ion and concurrently the sediment of the microbes immobilizing carrier to which the iron oxidizing microbes have attached is recovered and then reintroduced into the reactor in the step (a).

14 Claims, 4 Drawing Sheets

US 8,859,249 B2

PROCESS OF TREATMENT FOR OXIDIZING AN ACIDIC SOLUTION CONTAINING AN IODIDE ION AND AN IRON (II) ION

TECHNICAL FIELD

The present invention relates to a method of preparing an acidic solution containing an iron (III) ion produced by iron oxidizing microbes, and especially, it is applied to leaching copper from a copper sulfide ore using an iodide ion and an iron (III) ion.

BACKGROUND ART

In general, the following forms of leaching copper from a copper sulfide ore by a hydrometallurgical process are known: a form of leaching by a batch-wise stirring reaction using sulfuric acid or hydrochloric acid; a form of leaching by preparing a heap of the ore, providing sulfuric acid or hydrochloric acid to the top of the heap and recovering the liquid dropped by gravity (heap-leaching method); and the like. Also known is a method by utilizing the ability of bacteria such as iron oxidizing microbes for leaching and recovering the copper efficiently (bioleaching).

As for the hydrometallurgical process of the copper sulfide ore, a bioleaching method and the like have been put to practical use for a secondary copper sulfide ore such as chalcocite, covelline and the like. On the other hand, there is a problem that as the solubility of a primary copper sulfide ore such as chalcopyrite to mineral acids is very low, the leaching rate thereof is very low when the leaching is performed at ordinary room temperature.

With regard to the above-described problem, Japanese Patent Application No. 2009-193197 (Patent Document 1) which has not yet been laid open, reports the example that the leaching of a copper sulfide ore mainly including chalcopyrite and enargite is promoted at ordinary room temperature in the presence of an iodide ion together with an iron (III) ion as an oxidizing reagent. In the leaching, it is also desirable economically to prepare and provide the iron (III) ion used as an oxidizing reagent by oxidizing with the iron oxidizing microbes an iron (II) ion obtained as the result of the leaching reaction or inexpensive ferrous sulfate.

It is also desirable economically and environmentally that the post-leaching solution is reused as a leaching solution repeatedly without being discarded. However, it had been difficult to reproduce the iron (III) ion by using the iron oxidizing microbes in said leaching wherein a solution containing iodide ion is used. This is because there had been a problem that the iodide ion is converted into a molecular iodine, triiodide ion and the like, which prevent the iron oxidizing microbes from oxidizing iron and inhibit the proliferation of said microbes, In Japanese Patent Application No. 2010-060037, which has not yet been laid open, the applicant of the present application then proposed a method, wherein the iron (II) ion in the solution is oxidized into the iron (III) ion by the iron oxidizing microbes, after decreasing an amount of the iodine(s) in the post-leaching solution by using activated carbon.

Furthermore, in Japanese Patent Application No. 2010-128300 (Patent document 3), which has not yet been laid open, the applicant of the present application reported a method wherein the activated carbon and the iron oxidizing bacteria are used in the same reaction system, and thus, the oxidation of the iron (II) ion and the adsorption of the iodine(s) by the activated carbon are performed simultaneously.

Apart from the above-described field, Japanese Patent Application Publication No. S47-38981 (Patent document 4) reports an example of a reactor for continuously oxidizing iron in which iron oxide sludge is used as an immobilizing carrier for the iron oxidizing microbes. However, in said document, the invention is applied to treating acidic mine water containing an iron (II) ion in a sulfur mine and the like, but not studied for applying it to treating the leaching solution containing the iodide ion.

PRIOR ART DOCUMENTS

Patent Documents

[Patent document 1] Japanese Patent Appln No. 2009-193197
[Patent document 2] Japanese Patent Appln No. 2010-060037
[Patent document 3] Japanese Patent Appln No. 2010-128300
[Patent document 4] Japanese Patent Appln Publication No. S47-38981

OUTLINE OF INVENTION

Problem to be Solved by the Invention

As described above, for leaching copper efficiently from the copper sulfide ore mainly including chalcopyrite and enargite, the iodide ion and the iron (III) ion are essential. However, there is a problem that it is difficult to reproduce the iron (III) ion and circulate the leaching solution by using the iron oxidizing microbes due to the effect of iodine which prevents the iron oxidizing microbes from oxidizing iron and proliferating. Furthermore, although the method described in Japanese Patent Application No. 2010-060037 makes it possible to oxidize the iron (II) ion into the iron (III) ion, it is necessary to decrease the concentration of total iodine to less than 1 mg/L. Moreover, although the method described in Japanese Patent Application No. 2010-128300 makes it possible to afford higher concentration of iodine compared to the above-described method, it is necessary to use the activated carbon in the same reaction system as that of the iron oxidizing microbes. There was also a problem that when the iodine was adsorbed beyond the adsorbability of the activated carbon, said activated carbon must be recovered from the reaction system and be recycled. In addition, the Examples described in Japanese Patent Application Nos. 2010-060037 and 2010-128300 indicate implementing the methods under batch operation, and thus, it had not yet been studied whether the microbes can oxidize the iron under continuous operation such as adding the iron (II) ion continuously.

Accordingly, in the light of the above-described problems, one object of the present invention is to provide a method performing efficiently the oxidative treatment in the acidic solution containing the iodide ion and the iron (II) ion by using microbes, under the versatile and practical operative condition, in the leaching using the iodide ion. Another object of the present invention is to apply the present methods to leaching copper from the copper sulfide ore.

Means for Solving Problem

As a result of intense study by the present inventors for solving the above-described problems, it was found that when the acidic solution containing the iodide ion and the iron (II) ion was reacted in a reactor containing Jarosite and the iron oxidizing microbes attached to the same, the iron (II) ion in said solution can be oxidized continuously to the iron (III) ion by the iron oxidizing microbes. Thereby, the present invention was completed.

Namely, the present invention includes the following inventions.

(1) A method for oxidizing an iron (II) ion in an acidic solution containing an iodide ion and the iron (II) ion, the method comprising performing following steps (a)-(b) repeatedly and continuously:
(a) a step wherein the iron (II) ion in the acidic solution containing the iodide ion and the iron (II) ion is oxidized into an iron (III) ion in a reactor using a microbes immobilizing carrier to which iron oxidizing microbes have been attached;
(b) a step wherein sedimentation of the solution obtained in the step (a) is performed in a sedimentation tank to obtain the solution containing the iron (III) ion and concurrently the sediment of the microbes immobilizing carrier to which said iron oxidizing microbes have been attached is recovered and then introduced into the reactor in the step (a).
(2) The method according to (1), wherein the concentration of total iodine in said acidic solution containing the iodide ion and the iron (II) ion is about 4 mg/L or less.
(3) The method according to (1) or (2), wherein said reactor is a fluidized-bed reactor and the concentration of the microbes immobilizing carrier in the fluidized-bed is from about 10 g/L to about 300 g/L.
(4) The method according to any one of (1)-(3), wherein the particle size of said microbes immobilizing carrier is from about 0.2 µm to about 20 µm.
(5) The method according to any one of (1)-(4), wherein said microbes immobilizing carrier is a ferruginous mineral.
(6) The method according to any one of (1)-(5), wherein said microbes immobilizing carrier is Jarosite.
(7) The method according to any one of (1)-(6), wherein the iron oxidizing microbes are *Acidithiobacillus ferrooxidans*, the method being performed under atmospheric pressure.
(8) The method according to any one of (1)-(7), wherein the concentration of the iron (II) ion in said acidic solution containing the iodide ion and the iron (II) ion is from about 0.2 g/L to about 10 g/L.
(9) The method according to any one of (1)-(8), wherein said acidic solution containing the iodide ion and the iron (II) ion is a post-leaching solution, which is obtained via the step wherein copper is leached from a copper sulfide ore using a sulfuric acid solution containing an iodide ion and an iron (III) ion as a leaching solution.
(10) The method according to any one of claims 1-9, prior to said steps (a)-(b), further comprising a step wherein said acidic solution containing the iodide ion and the iron (II) ion is treated with activated carbon to adsorb the iodine.
(11) The method according to (10), further comprising a step wherein the following solutions are mixed and used as a leaching solution for a copper sulfide ore:
the solution obtained in said step (b) containing the iron (III) ion;
the solution containing iodine recovered by treating said activated carbon to which the iodine had been adsorbed with a solution containing a sulfite ion.

Effect of the Invention

According to the method of the present invention,
(1) The solution containing the iron (III) ion can be efficiently prepared from the acidic solution containing the iodide ion and the iron (II) ion. Namely, as a carrier for immobilizing the iron oxidizing microbes, a ferruginous mineral (preferably Jarosite) is used for oxidizing iron, and then the foregoing ferruginous mineral is recovered by sedimentation to be added into the iron oxidizing reactor again. Thereby, the concentration of the iron oxidizing microbes in the reactor can be retained at high level. As the result, even if a solution contains the iodine, which is inhibitory against the growth of the iron oxidizing microbes, at higher concentration than in the conventional batch operation, the iron (III) ion can be efficiently prepared.

(2) In addition, it is shown to be possible to perform continuously the process of oxidizing the iron which was conventionally performed in batch operation. The iron (II) ion, which is necessary for proliferation of the iron oxidizing microbes, is continuously provided, and thus, the proliferation of the iron oxidizing microbes which require the iron (II) ion as source of nutrient is preferably promoted. As the result, the concentration of the iron oxidizing microbes in the reactor can be kept at high level, and therefore, even if a solution contains the iodine, which is inhibitory against the growth of the iron oxidizing microbes, at higher concentration than in the conventional batch operation, the iron (III) ion can be efficiently prepared.

(3) By applying the above-described means to the leaching copper from the copper sulfide ore with a sulfuric acid solution containing the iodide ion and the iron (III) ion as a leaching solution, the copper can be leached efficiently at low cost from the copper sulfide ore including chalcopyrite and enargite.

MODES FOR CARRYING OUT THE INVENTION

1. Outline and Definitions

One embodiment of the present invention is the method of treating the acidic solution containing the iodide ion and the iron (II) ion. The features of the present invention are (1) producing the iron (III) ion by aerobically reacting the acidic solution containing the iodide ion and the iron (II) ion in the iron oxidizing reactor containing the microbes immobilizing carrier to which the iron oxidizing microbes had attached; and (2) concurrently, recovering said carrier via the sedimentation to introduce into the reactor again. Thereby, (3) the iron oxidizing process is performed in a continuous operation, and thus, (4) the concentration of the iron oxidizing microbes in the reactor is kept at high level, and (5) the iron (II) ion required for proliferation of the iron oxidizing microbes is continuously provided, and (6) the preferable condition for the proliferation of the iron oxidizing microbes is kept, and (7) thereby, the solution containing the iron (II) ion can be stably oxidized even in the presence of the iodine which has an inhibitory effect against the proliferation of the iron oxidizing microbes.

Another embodiment of the present invention is characterized in that the solution containing the produced iron (III) ion are mixed with an aqueous solution containing the iodine recovered after adsorption to the activated carbon, and then the mixture is used as a solution for leaching copper from the copper sulfide ore.

The term "iodide ion" used herein means an ion represented by "$I^-$", and the term "triiodide ion" used herein means an ion represented by "$I_3^-$", and the term "molecular iodine" used herein means a molecule represented by "$I_2$". Furthermore, the term "iodine" described herein means elemental iodine in any state including the above-described "$I^-$", "$I_3^-$", "$I_2$" and the like. Accordingly, the term "concentration of iodine" described herein means the total concentration of iodine which includes not only molecular iodine ($I_2$) but also any state of iodine such as iodide ion ($I^-$), triiodide ion ($I_3^-$) and the like.

2. Process Flow Diagram

Figure 2:
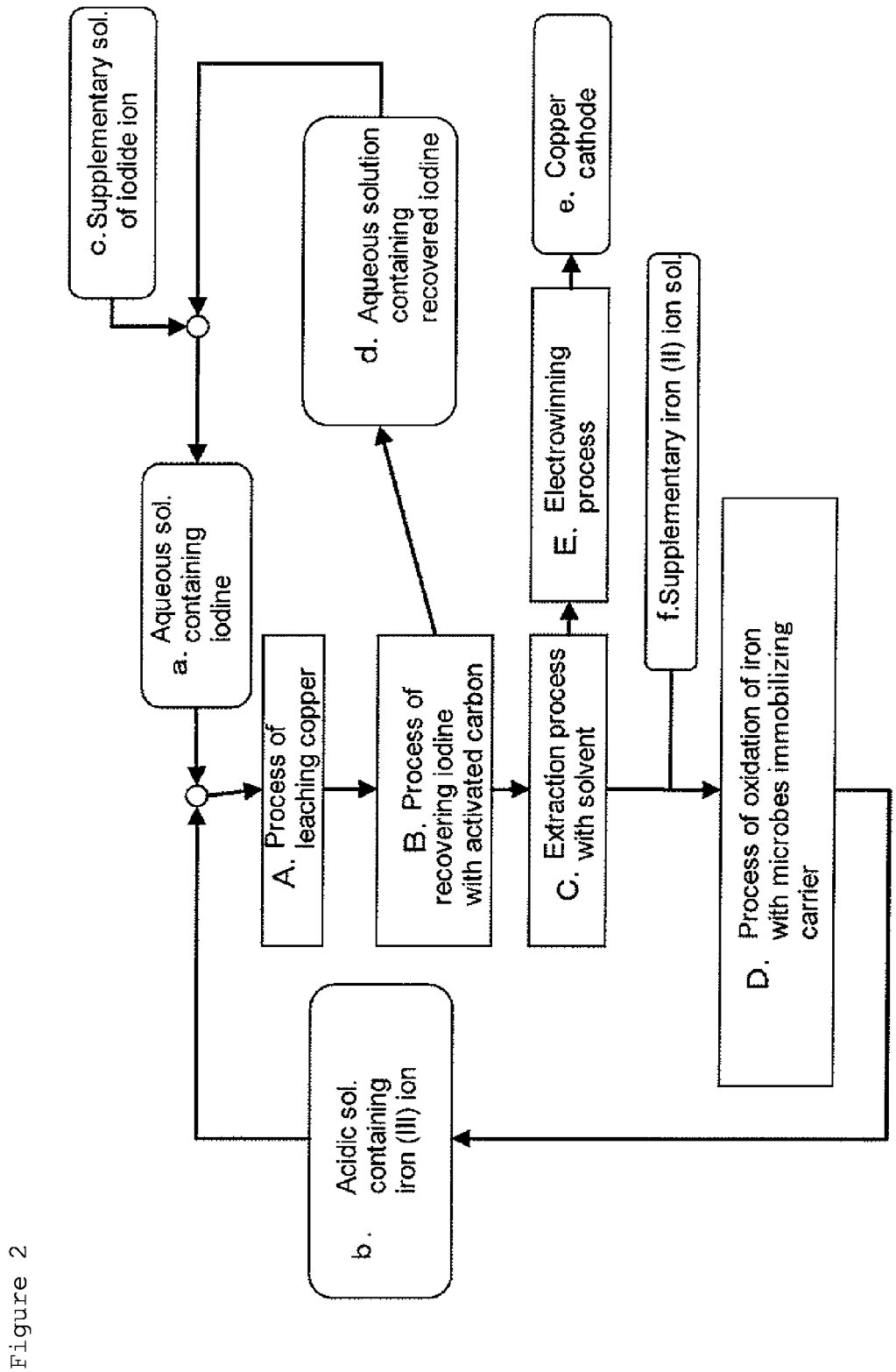
FIG. 2 This figure shows the flow of treatment using in the reactor the microbes immobilizing carrier to which the iron oxidizing microbes had been attached in the process of treating the solution containing the iodide ion and the iron (II) ion.

The present invention can be used, for example, by integrating it into the process flow described in FIG. 2 as a part of the process. Each process is explained hereinafter.

2-1. Process of Leaching Copper (FIG. 2 A)

The method according to the present invention may be applied to several leaching forms such as a hydrometallurgical process of copper wherein a sulfuric acid solution is used as a leaching solution. For example, the method may be not only a batch-wise stirring leaching, but also any of heap-leaching or dump-leaching wherein a sulfuric acid is supplied over accumulated ores so that copper is leached into the sulfuric acid.

2-1-1. Objective Mineral

The copper sulfide ore including chalcopyrite or enargite, which is an objective ore of the above-described process for leaching copper, may be a copper sulfide ore mainly including chalcopyrite or enargite, or a copper sulfide ore partly including chalcopyrite or enargite. The content thereof is not limited to the particularly defined content. The copper sulfide ore is preferably a copper sulfide ore mainly including chalcopyrite or enargite, in view of the sufficient effect of leaching copper by the method according to the present invention.

2-1-2. Temperature Condition

The temperature at the leaching is not limited to the particularly defined temperature. The leaching can be carried out at ordinary room temperature, and heating or any other treatment is not necessary.

2-1-3. Leaching Solution

The solution used for dissolving and leaching the copper from the copper sulfide ore may be, for example, the leaching solution containing sulfuric acid, the iron (III) ion and the iodide ion ($I^-$). It is considered that the dissolving and leaching of the copper sulfide ore by using said leaching solution proceed under a series of catalytic reactions by iodine indicated in the following Formula 1 and Formula 2.

$2I^- + 2Fe^{3+} \rightarrow I_2 + 2Fe^{2+}$ (Formula 1)

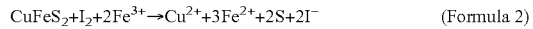

$CuFeS_2 + I_2 + 2Fe^{3+} \rightarrow Cu^{2+} + 3Fe^{2+} + 2S + 2I^-$ (Formula 2)

It is understood that when each side of (Formula 1) and (Formula 2) are combined respectively, and thus iodine ($I_2$) components are deleted, the following (Formula 3) is obtained which has been conventionally proposed to show the leaching reaction for the copper sulfide ore by the iron (III) ion as an oxidizing agent.

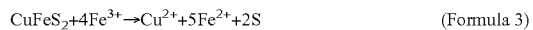

$CuFeS_2 + 4Fe^{3+} \rightarrow Cu^{2+} + 5Fe^{2+} + 2S$ (Formula 3)

First, during the reaction shown in Formula (I), the iodide ion ($I^-$) added to the leaching solution is oxidized by the iron (III) ion ($Fe^{3+}$) to produce the molecular iodine ($I_2$). A simple substance of the iodine ($I_2$) produced in the reaction is further reacted with the remaining iodide ion ($I^-$), and thus the triiodide ion ($I_3^-$) is also produced in the leaching solution. Total concentration of iodine in the leaching solution may be properly decided according to reaction form, type, shape and copper grade of the objective copper sulfide ore and any other conditions. However, it is preferably about 100 mg/L—about 300 mg/L indicated in Japanese Patent Application Public Disclosure No. 2010-189258 or about 8 mg/L—about 100 mg/L indicated in Japanese Patent Application No. 2009-193197.

2-2. Process for Oxidizing Iron Using the Microbes Immobilizing Carrier (FIG. 2 D)

As indicated in Formula (3), for leaching the copper sulfide ore, it is necessary to provide the corresponding amount of the iron (III) ion as an oxidizing agent. For continuous leaching of the copper sulfide ore, it is necessary to provide continuously the iron (III) iron as an oxidizing agent. For purpose of these, it is ideal to produce Fe (III) ion from Fe (II) ion by using the iron oxidizing microbes or to produce Fe (III) ion by adding the inexpensive ferrous sulfate and the like (FIG. 2 f).

However, the iodine has an inhibitory effect against the growth of the iron oxidizing microbes. Especially, when the iron oxidizing microbes are used, the iodide ion which does not exhibit a strong inhibitory effect against the growth of microbes is also oxidized by the iron (III) iron generated, and thus converted into the molecular iodine ($I_2$) or the triiodide ion ($I_3^-$) both of which have a strong inhibitory effect against the growth of microbes. Therefore it is known to be difficult to produce the iron (III) ion by oxidizing the iron (II) ion contained in the solution after copper leaching process or the iron (II) ion added as the ferrous sulfate and the like using the iron oxidizing microbe.

One embodiment of the present invention provides the method for continuously producing the iron (III) ion,
wherein the microbes immobilizing carrier to which the iron oxidizing microbes have been attached is used,
wherein the carrier is recovered via sedimentation after the iron oxidation and reintroduced again into the iron oxidizing reactor,
whereby the iron oxidation, which is conventionally preformed in a batch operation, is continuously performed,
whereby the concentration of the microbes in the reactor is kept at high level,
and wherein the iron (II) ion, which is necessary for proliferation of the microbes, is concurrently provided continuously to retain preferable environment for their proliferation. As a result, even in the presence of the iodiine molecule ($I_2$) and/or the triiodide ion ($I_3^-$) which are inhibitory for their proliferation, the iron (III) can be stably produced.

2-2-1. Iron Oxidizing Microbes

The iron oxidizing microbes used for reproduction of the iron (III) ion from the iron (II) ion is not limited to specific genus or species, provided that the microbes have an ability of oxidizing iron. Concretely, the microbes may be *Acidithiobacillus ferrooxidans*, *Acidimicrobium ferrooxidans*, microbes belonging to the genus of *Leptosprillum*, microbes belonging to *Ferroplasma*, or microbes belonging to *Acidiplasma*.

Among them, *Acidithiobacillus ferrooxidans* is effective in the present invention due to its ability to oxidize the iron at normal temperature and pressure. As one example, *Acidithiobacillus ferrooxidans* FTH6B deposited to National Institute of Technology and Evaluation Patent Microorganisms Depositary, (Deposition No. NITE BP-780) may be used.

The temperature and pressure for the iron oxidation reaction by the iron oxidizing microbes may be optimized according to the microbes.

When said *Acidithiobacillus ferrooxidans* is used, it is preferred to perform under atmospheric pressure at about 20° C.-about 40° C.

2-2-2. Microbes Immobilizing Carrier

Said iron oxidizing microbes are immobilized onto the microbes immobilizing carrier for use of the reaction of iron oxidation. The microbes immobilizing carrier for iron oxidizing microbes is preferably a ferruginous mineral because of reasons such as their well growth in the mineral. The ferruginous mineral used in the present invention is desirably a secondary ferruginous mineral having a hydrophilic surface such as iron oxide (such as magnetite, and hematite) and sulfate (such as Jarosite, and Schwertmannite), and especially, Jarosite is desirable.

These can be a natural mineral or mineral chemically synthesized and/or prepared. It is also possible to prepare Jarosite, Schwertmannite and the like by cultivating an iron oxidizing bacteria in a medium containing an iron (II) ion.

Particle size of the ferruginous mineral need to be a constant size of fine granule. For example, the size is preferably about 0.2-20 and more preferably about 1-10 μm, because the greater the surface area is, the more iron oxidizing bacteria can be distributed and set on the mineral, leading to effective oxidation reaction of iron. By "particle size" described herein is meant the size measured by Laser Diffraction Particle Size Analyzer. Concretely, SALD-2100 available from Shimazu Corporation was used. Furthermore, the concentration of the ferruginous mineral is preferably about 10-300 g/L in the below-mentioned reactor, and more preferably about 100-200 g/L.

2-2-3. Immobilizing the Iron Oxidizing Microbes onto the Ferruginous Mineral The microbes can be immobilized onto the ferruginous mineral by mixing the ferruginous mineral and the microbes, for certain time, at normal temperature or the temperature suitable for growth of the microbes.

Without any particular agent and treatment, the microbes can be immobilized by adding the ferruginous mineral into the culture solution of the iron oxidizing microbes and then mixing/stirring the culture solution at the temperature suitable for growth of the microbes.

With regard to Jarosite, and Schwertmannite, the minerals can be prepared by using the iron oxidizing microbes, concurrently with the microbes being attached/immobilized onto the minerals.

Alternatively, if the mineral is a natural mineral or a chemically-synthesized mineral, the microbes can be immobilized onto the mineral by adding the mineral into the culture medium of the iron oxidizing microbes and then mixing/stirring the medium at the temperature suitable for growth of the microbes.

With regard to the ferruginous mineral such as magnetite, hematite and the like which the microbes do not produce during the cultivation, the microbes can be also immobilized onto the mineral by adding the mineral into the culture solution of the iron oxidizing microbes and then mixing/stirring the solution at the temperature suitable for growth of the microbes.

2-2-4. Reactor and Sedimentation Tank (FIG. 3)

Said oxidation process using the microbes immobilizing carrier to which the iron oxidizing microbes have been attached may be performed in a reactor, preferably a fluidized bed reactor. FIG. 3 indicates one example of the fluidized bed reactor for performing said oxidation process.

Figure 3:
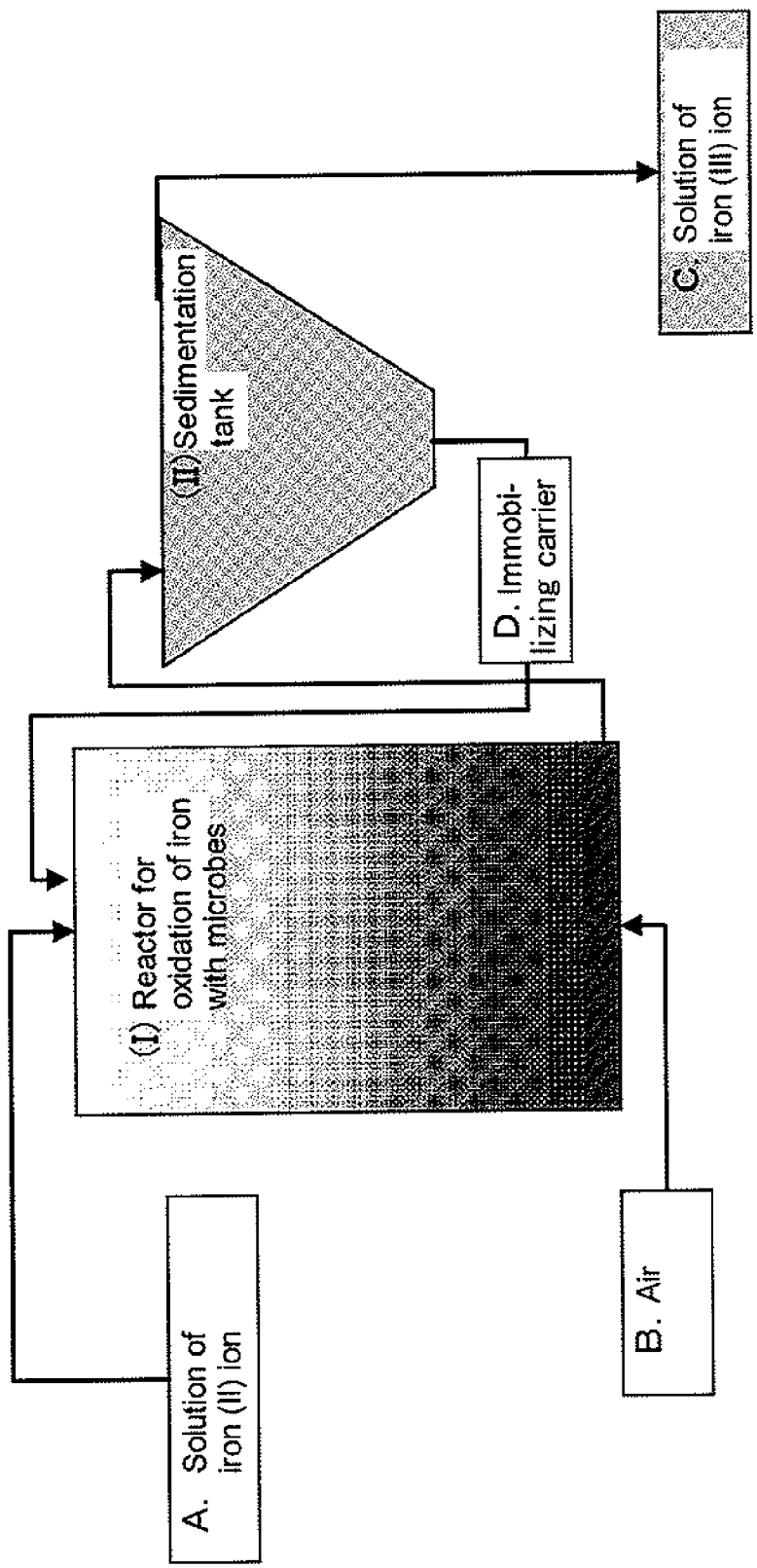
FIG. 3 This figure shows the process flow diagram indicating the process for oxidizing the iron and sedimentation tank with the use of the microbes immobilizing carrier to which the iron oxidizing microbes had been attached.

In the fluidized bed reactor (FIG. 3, (I)), the microbes immobilizing carrier to which the iron oxidizing microbes had been attached has been introduced in advance. The acidic solution containing the iodide ion and the iron (II) ion (FIG. 3A) (e.g., the post-leaching solution obtained from the process wherein copper is leached from the copper sulfide ore using the sulfuric acid solution as leaching solution as described above) is added into the reactor, and further, air is introduced from the lower part (FIG. 3B). Then, in said reactor, the oxidation reaction of iron (II) ion is performed by the iron oxidizing microbes, producing the iron (III) ion.

After said oxidation process, the solution is transferred to the sedimentation tank (FIG. 3 (II)), in which sedimentation is carried out. By the sedimentation, the ferruginous mineral onto which the iron oxidizing microbes have been attached is obtained as the sediment. Said sediment is recovered from the sedimentation tank (FIG. 3D), and may be reintroduced into the reactor for reuse in the iron oxidation process. From the supernatant, a solution containing the iron (III) ion (FIG. 3C) which is produced in said reactor is obtained, said solution being able to be used in the above-described process for leaching copper.

The concentration of iodine in the solution prior to the treatment in the reactor according to the present invention is preferably, but not limited to, about 4 mg/L or less for the better oxidation process. The lower limit thereof is typically, but not limited to, not less than about 0.5 mg/L or not less than about 1.0 mg/L.

The concentration of the iron (II) ion in the solution treated in the reactor according to the present invention is, but not limited to, preferably the range which is about 0.2 g/L to about 10 g/L, and more preferably from about 1 g/L to about 7 g/L. The retention time is preferably from about 1 hour to about 48 hours. The range of pH is preferably from about 0.5 to about 4.

These ranges of the concentration of the iron (II) ion and the retention time are also suitable one as the concentration of the iron (II) ion in the post-leaching solution from the copper sulfide ore, and the concentration of the iron (II) ion necessary for the leaching solution of the copper sulfide ore prepared by mixing the solution containing the generated iron (III) ion and a solution containing iodine.

As for other conditions, the reaction temperature is preferably from about 10° C. to about 50° C. In addition, the rate of introducing air into the reactor is preferably at the rate of from about 0.1 v/v/min to about 5 v/v/min.

2-2-5. Continuous Process

By performing a series of the following steps (i) to (iii) continuously, continuous operation of the iron oxidation process, which was conventionally performed in a batch operation, can be realized and thereby the concentration of the bacteria in the reactor can be retained at high level: (i) a step of the iron oxidation reaction in the reactor; (ii) a step of recovering the ferruginous mineral (to which the iron oxidizing microbes attach) in the sedimentation tank; and (iii) a step of introducing the recovered ferruginous mineral into the reactor. Furthermore, the continuous supply of the iron (II) ion necessary for growth of the iron oxidizing microbes promotes the preferable growth of the iron oxidizing microbes to maintain the high concentration of the microbes in the reactor. Then, maintaining the high concentration of the microbes in the reactor can reduce the above-described negative effect by the iodine and the like.

2-3. Process of Recovering Iodine with Activated Carbon

Accordingly, by using the above-described method, the iron (II) ion in the solution containing the iodine and the iron (II) ion can be oxidized even in the presence of the iodine. However, the concentration of iodine in the solution may be reduced prior to the process of oxidation of iron, for the purpose of promoting the better oxidation reaction of iron.

2-3-1. Process of Treatment with Activated Carbon (FIG. 2B)

While there is a process using activated carbon for reducing the concentration of iodine, other solids having a hydrophobic surface may be used such as coke, and a hydrophobic resin. However, the activated carbon is particularly excellent because it has high specific surface area and high ability of removing iodine.

Although the type, source and any other properties of the activated carbon used in the present invention are not limited, the activated carbon preferably have wide surface area, is preferably suitable for use in liquid phase, and is preferably excellent in their stability. The shape thereof is preferably granular or spherical. Examples include Coconut Shell Mc available from Taihei Chemical Industrial Co., Ltd. SHIRASAGI X7000H available from Japan EnviroChemicals, Ltd. and the like.

2-3-2. Process for Recovering Iodine

From the activated carbon to which the iodine has been adsorbed in the above-described process, the iodine can be recovered by treatment such as a chemical solution, heating, and burning (FIG. 2d). Concretely, the activated carbon is treated with a solution containing a sulfite ion for elution, and thus, the iodine is separated from the activated carbon in the form of an iodide ion and recovered in the form of a solution thereof. It is preferable to recover the iodine using a solution containing about 1-100 times of the sulfite ion by weight relative to the iodine to be eluted. The solution containing the recovered iodine may be used as the leaching solution for the process of leaching copper. Another iodide ion may be optionally supplemented to the aqueous solution containing iodine, in addition to the iodine recovered (FIG. 2c). Further, said aqueous solution containing iodine may be mixed with the solution containing the iron (III) ion obtained from said process of oxidation of iron and then used as the leaching solution for the process of leaching copper (FIG. 2a).

2-4. Process of Recovering Copper (FIG. 2C, E, e)

When copper is recovered from the solution after the process of leaching copper, solvent extraction method is generally used wherein extractant is used to extract the copper selectively while cementation method is rarely used. These methods may be used at any stage such as before or after the process for recovering iodine and/or oxidizing iron according to the present invention.

3. The Others

The process is not necessarily to be a serial flow as indicated in FIG. 2. The process may be parallel such as bypassing the process of extracting copper or the process for recovering iodine and oxidizing iron.

In practice, any optimal process flow may be applied in consideration of several influences such as inhibitory action of the iodine against the extracting agent, and toxicity of the extracting agent against the microbes.

EXAMPLES

The present invention will be further explained concretely via examples hereinafter. However, it should be noted that said examples do not restrict the present invention.

1. Method of Determination

Concentrations of copper and iron in a solution were determined with ICP atomic emission spectrometer (ICP-AES, Seiko Instruments Inc., SPS7700). Concentration of iron (II) ion was determined with redox titration method using potassium dichromate. Concentration of iron (III) ion was calculated from the difference between the concentration of whole iron determined with ICP-AES and the concentration of iron (II) ion. Concentration of iodine was determined by selective ion electrode method. Concretely, all of iodine existing as molecular iodine ($I_2$) and triiodide ion ($I_3^-$) were reduced to iodide ion by appropriately adding zinc powder, and in the same way, all of iron (III) ion were reduced to iron (II) ion, and then, the concentration is determined with the iodide selective electrode. In order to eliminate interference by the iron ion, citric acid, which is chelating agent, was used for masking the iron (II) ion. For determining concentration of microbes, ultrasonic cleaning of Jarosite in the reactor was performed for 10 minutes and then 10-fold dilution with dilute sulfuric acid of pH 2 was repeated 3 times to obtain 1000-fold diluted solution. Concentration of microbes was determined by microscopy of said diluted solution on Thoma hemacytometer. Particle size of Jarosite was determined with laser diffraction particle analyzer (Shimadzu Corporation, SALD-2100).

2. Post-Leaching Solution Containing Iodide Ion and Iron (II) Ion

As an ore, a copper sulfide ore mined in Caserones in Chile was used. The leaching solution included potassium iodide and iron (III) sulfate, pH of which was adjusted with sulfuric acid. Said leaching solution was provided in drops using a pump for performing the leaching reaction and then the recovered leaching solution was used as a post-leaching solution.

The post-leaching solution from the process of leaching copper was provided into the column of activated carbon to reduce the concentration of iodine, and then, iron powder cementation method was applied as process of elimination of copper to reduce the concentration of copper. Subsequently, into said solution, ferrous sulfate and concentrated (conc.) sulfuric acid were added.

The post-leaching solution obtained from the above-described process included 1 g/L or less of copper, 4 g/L of iron (II) ion, and pH of which solution was 1.8. The concentration of the whole iron in the solution was 4 g/L. Accordingly, oxidation rate of the iron was 0% before said post-leaching solution was introduced into the reactor described below. During implementation term of said process, the concentration of iodine varied within the range from 1.5 mg/L to 6 mg/L. The change of the concentration of the iodine was caused by insufficient elimination of the iodine by the activated carbon.

3. Iron Oxidizing Microbes and Microbes Immobilizing Carrier

Figure 1:
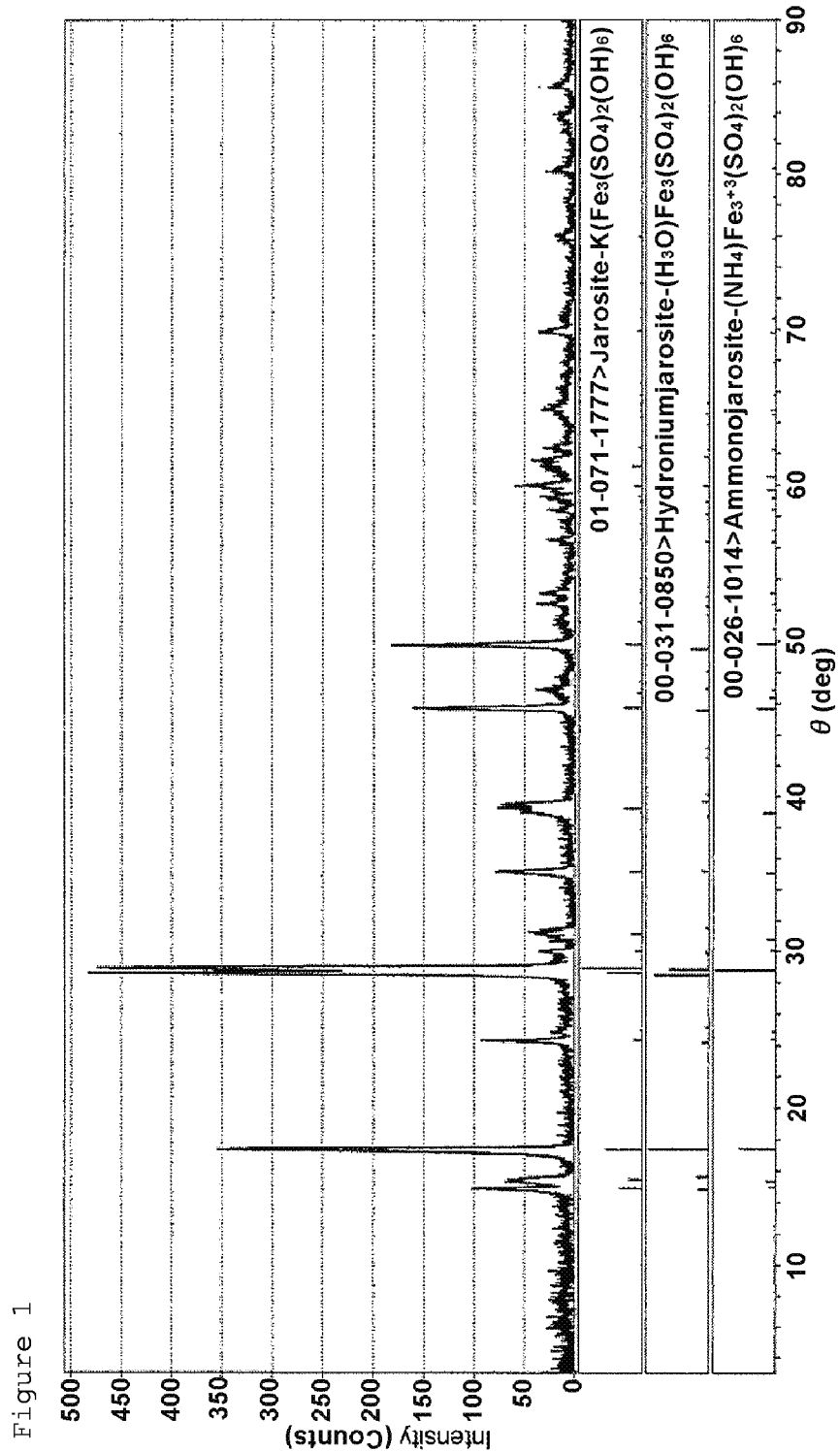
FIG. 1 Data of XRD (X-ray differaction) analysis of Jarosite used as the carrier for immobilizing the iron oxidizing microbes according to the present invention.

Jarosite as a microbes immobilizing carrier was obtained in the form of the precipitate produced by batch culture of the iron oxidizing microbe, *Acidithiobacillus ferrooxidans* FTH6B (NITE BP-780). Said precipitate was confirmed to be Jarosite by XRD shown in FIG. 1 prior to the subsequent test. The average of particle size of Jarosite obtained was 1.6 µm.

4. Process of Oxidation of Iron

In the process of oxidation of the iron, a fluidized bed reactor (volume 2.2 L) was used for performing oxidation process. Concentration of Jarosite in the reactor was adjusted to 150 g/L. When starting culture, *Acidithiobacillus ferrooxi-*

*dans* FTH6B (NITE BP-780) was added at the concentration of $2.0 \times 10^8$ cells/ml without any particular treatment such as aseptic treatment.

Air was introduced into the reactor from the bottom thereof at rate of 1 v/v/min (2 L/min). With the temperature being kept at 30° C., the acidic solution at pH 1.8 containing said iron (II) ion (4 g/L) was added under the atmospheric pressure at the rate within the range of from 1 L/h to 4 L/h. When air was added at rate of 1 v/v/min, the amount of air added was 2.2 L/min because the volume of the reactor was 2.2 L. The average retention time of said acidic solution in the reactor was 42 hours.

For recovering Jarosite to which the iron oxidizing microbes were attached after the process of oxidation of iron, a sedimentation tank (volume 0.5 L) was equipped.

The sediment in a slurry state obtained in the sedimentation tank was reintroduced into the reactor again. The rate of said introduction was ¼ of addition rate of the acidic solution with pH 1.8 containing said iron (II) ion (4 g/L). An outline of the flow from the process of oxidation of iron to the sedimentation tank is shown in FIG. 3.

5. Concentration of the Microbes in the Reactor

The average of concentration of the microbes in the reactor for 58 days was $1.2 \times 10^{11} \pm 2.7 \times 10^{10}$ cells/ml, which shows that when Jarosite is used as the immobilizing carrier for the iron oxidizing microbes, the higher concentration of the microbes in the reactor can be maintained compared to the concentration of the microbes $1.0\text{-}4.0 \times 10^8$ cells/ml which is usually obtained in the liquid culture.

6. Oxidation Rate of Iron and Concentration of Iodine after the Reaction

Figure 4:
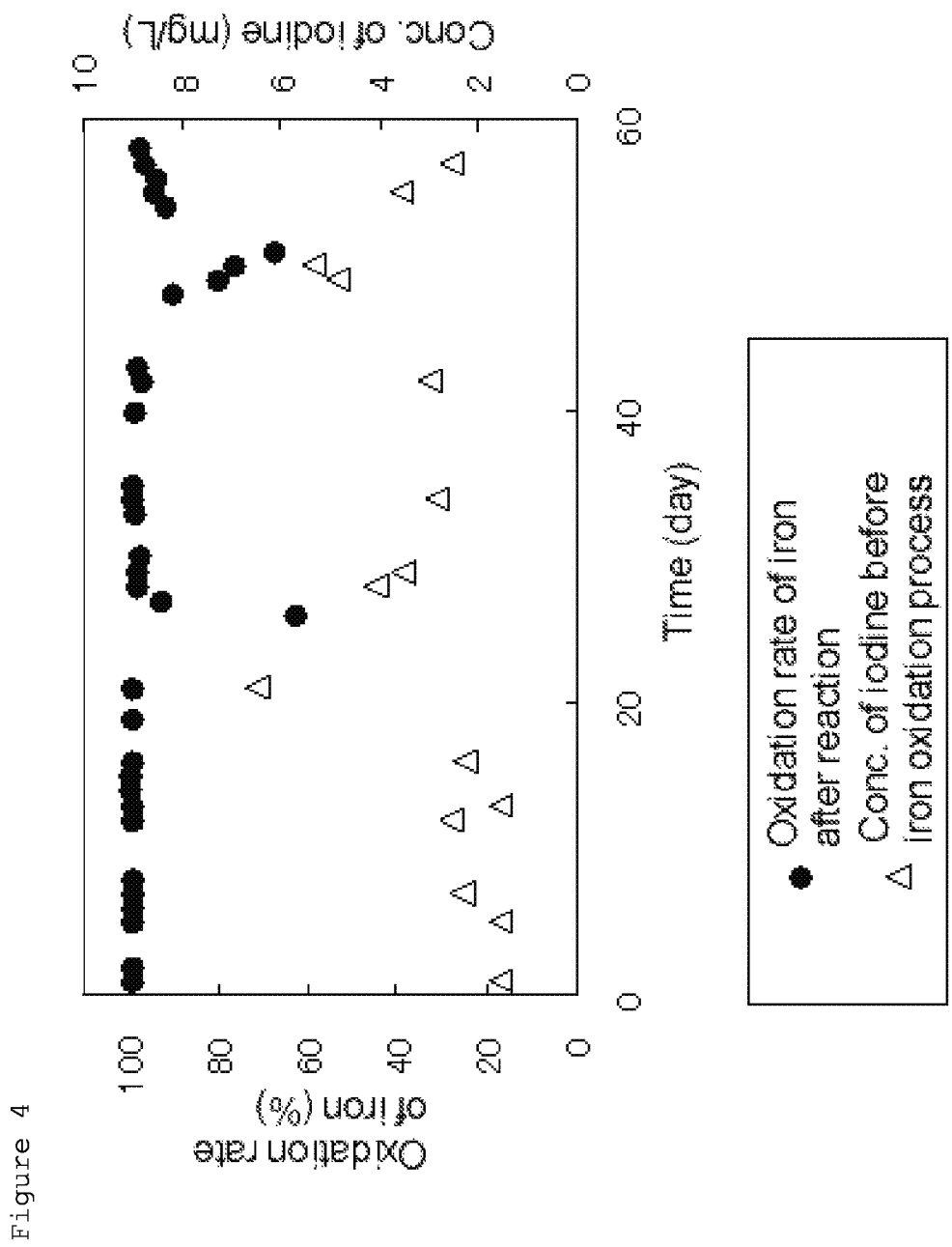
FIG. 4 This figure shows time-course of changes in the oxidization rate of iron and the concentration of iodine.

FIG. 4 shows oxidation rate of iron calculated from the concentration of iron (III) ion after the reaction and the concentration of iodine before the iron oxidation process.

As the result, it was revealed that when Jarosite is used as the immobilizing carrier for the iron oxidizing microbes, the concentration of microbes can be maintained at high level, and thus using said reactor, the iron (III) ion can be stably produced even if the iodine is present in the solution before the iron oxidation process. Especially, in the case where the concentration of iodine is 4 mg/L or less, the oxidation rate of iron was shown to be nearly 100%.

This is more advantageous in that higher concentration of iodine is acceptable with compared to the reaction described in prior Japanese patent application No. 2010-060037 wherein the oxidation of iron may not proceed unless the concentration of iodine is 1 mg/L or less. Furthermore, it is not necessary to consider the limit of adsorbability of the activated carbon for iodine, because the oxidation process of the iron and the process of removing the iodine are not performed simultaneously, unlike the processes in Japanese patent application No. 2010-128300.

7. Effect of Continuous Operation

In the prior patent, said oxidation process of iron and sedimentation process were performed in batch operation. To the contrary, these results seem to be caused from the fact that in the present invention, continuous operation is used, and thereby, supplying continuously the iron (II) ion necessary for growth of the iron oxidizing microbes, and thereby increasing the upper-limit of concentration of iodine in the environment suitable for the growth of the iron oxidizing microbes.

Together with this, it is also indicated that the acidic solution containing the iodide ion and the iron (II) ion can be treated to produce efficiently and stably the iron (III) ion by maintaining the high concentration of the microbes in the reactor.

These working examples indicated that by reacting the acidic solution containing the iodide ion and the iron (II) ion in the reactor in which Jarosite is used as the immobilizing carrier for the iron oxidizing microbes, even in the presence of the iodine in said solution at the concentration of about 4 mg/L, the iron (II) ion in said solution can be oxidized to the iron (III) ion by the iron oxidizing microbes without being influenced inhibitorily against their growth from the molecular iodine ($I_2$) or triiodide ion ($I_3^-$).

In addition, it is also indicated that when a solution prepared by mixing an aqueous solution containing said iron (III) ion and an aqueous solution containing iodide ion is used for leaching from the copper sulfide ore, the leaching of copper from the copper sulfide ore can be promoted.

What is claimed is:

1. A method for oxidizing an iron (II) ion in an acidic solution containing an iodide ion and the iron (II) ion, the method comprising performing following steps (a)-(c) repeatedly and continuously: (a) contacting the acidic solution containing the iodide ion and the iron (II) ion with an iron-oxidizing microbe attached to a microbe-immobilizing carrier in a reactor to oxidize iron (II) to iron (III) and generate a solution, wherein the acidic solution containing the iodide ion and the iron (II) ion has a concentration of total iodine ranged from 1 mg/L to about 4 mg/L; (b) sedimenting the solution generated in step (a) in a sedimentation tank to obtain a solution containing the iron (III) ion and a sediment of the microbe-immobilizing carrier; and (c) reintroducing the sediment from step (b) into the reactor in the step (a): wherein said acidic solution containing the iodide ion and the iron (II) ion is a post-leaching solution which is obtained via a step wherein copper is leached from a copper sulfide ore using a sulfuric acid solution containing an iodide ion and an iron (III) ion as a leaching solution.

2. The method according to claim 1, wherein said reactor is a fluidized-bed reactor and the microbe-immobilizing carrier in a fluidized-bed has a concentration from about 10 g/L to about 300 g/L.

3. The method according to claim 1, wherein the microbe-immobilizing carrier has a particle size of from about 0.2 μm to about 20 μm.

4. The method according to claim 1, wherein said microbe-immobilizing carrier is a ferruginous mineral.

5. The method according to claim 1, wherein said microbe-immobilizing carrier is Jarosite.

6. The method according to claim 1, wherein the iron-oxidizing microbes are *Acidithiobacillus ferrooxidans*, the method being performed under atmospheric pressure.

7. The method according to claim 1, wherein the iron (II) ion in said acidic solution containing the iodide ion and the iron (II) ion has a concentration from about 0.2 g/L to about 10 g/L.

8. The method according to claim 1, wherein prior to said steps (a)- (b), said method further comprises a step wherein said acidic solution containing the iodide ion and the iron (II) ion is treated with activated carbon to adsorb iodine.

9. The method according to claim 8, further comprising a step of leaching a copper sulfide ore with a mixture of the following solutions:
   the solution obtained in said step (b) containing the iron (III) ion;
   a solution containing iodine recovered by treating said activated carbon to which the iodine had been adsorbed with a solution containing a sulfate ion.

10. The method according to claim 2, wherein the microbe-immobilizing carrier has a particle size of from about 0.2 μm to about 20 μm.

11. The method according to claim 2, wherein said microbe-immobilizing carrier is a ferruginous mineral.

12. The method according to claim 3, wherein said microbe-immobilizing carrier is a ferruginous mineral.

13. The method according to claim 2, wherein said microbe-immobilizing carrier is Jarosite.

14. The method according to claim 3, wherein said microbe-immobilizing carrier is Jarosite.

\* \* \* \* \*